(12) United States Patent
Bitterhof

(10) Patent No.: US 6,676,645 B1
(45) Date of Patent: Jan. 13, 2004

(54) BREAST-MILK ABSORBENT PAD

(75) Inventor: Andreas Bitterhof, Nattheim-Auernheim (DE)

(73) Assignee: Paul-Hartmann-Strasse AG, Heidenheim (DE)

(*) Notice: Subject to any disclaimer, the term of this patent is extended or adjusted under 35 U.S.C. 154(b) by 67 days.

(21) Appl. No.: 09/937,439

(22) PCT Filed: Sep. 27, 2001

(86) PCT No.: PCT/EP00/01716
§ 371 (c)(1),
(2), (4) Date: Sep. 27, 2001

(87) PCT Pub. No.: WO00/57931
PCT Pub. Date: Oct. 5, 2000

(30) Foreign Application Priority Data

Mar. 25, 1999 (DE) .......................... 199 13 478

(51) Int. Cl.$^7$ ................................ A61F 13/15
(52) U.S. Cl. ................ 604/385.07; 604/368; 604/367
(58) Field of Search ................ 604/385.07, 364, 604/367, 368, 369, 375, 376, 377

(56) References Cited

U.S. PATENT DOCUMENTS

| | | | | |
|---|---|---|---|---|
| 3,738,362 A | * | 6/1973 | Sneider ........................ 128/280 |
| 4,125,114 A | * | 11/1978 | Repke ......................... 128/280 |
| 4,193,404 A | * | 3/1980 | Repke et al. ................. 128/280 |
| 5,011,864 A | * | 4/1991 | Nielsen et al. ................ 521/70 |
| 5,073,202 A | * | 12/1991 | Wallach ......................... 134/6 |
| 5,149,336 A | * | 9/1992 | Clarke et al. ................. 604/388 |
| 5,599,916 A | * | 2/1997 | Dutkiewicz et al. .......... 536/20 |

FOREIGN PATENT DOCUMENTS

| | | | | |
|---|---|---|---|---|
| EP | 0 698385 | 2/1996 | | |
| EP | 0 816 405 | 1/1998 | | |
| EP | 0 844 270 | 5/1998 | | |
| GB | 977 708 | 12/1964 | | |
| GB | 2 292 526 | 2/1996 | | |
| GB | 2314856 | * | 1/1998 | ......... D21H/17/24 |
| JP | 05262990 | 10/1993 | | |
| WO | 92/16681 | 10/1992 | | |

* cited by examiner

Primary Examiner—Weilun Lo
Assistant Examiner—Jacqueline Stephens
(74) Attorney, Agent, or Firm—Young & Basile, PC

(57) ABSTRACT

A breast-milk absorbent pad includes an absorbent layer especially made of a fiber material and, optionally, with super-absorbent hydrogel materials, that absorbs liquids. The absorbent pad additionally includes chitosan to better use the absorbing capacity of the absorbent layer.

9 Claims, 1 Drawing Sheet

BREAST-MILK ABSORBENT PAD

BACKGROUND

The invention relates to a breast-milk absorbent pad having a fluid-absorbent layer, which is normally made from a fiber material and can optionally contain superabsorbent hydrogel materials to absorb and hold fluid. A breast-milk absorbent pad of this type is described, for example, in EP 0 698 385 A2.

Breast-milk absorbent pads are used to absorb breast milk that reflows in nursing mothers between nursing periods and to prevent clothing from becoming soiled. They are an aid to discretion. Furthermore, breast-milk absorbent pads are usually fitted with an inside surface which is soft and compatible with the skin in order not to create any skin irritation such as a piece of clothing might possibly cause to a breast made tender by nursing.

Mother's milk consists of fat in a proportion of 2 to 8 percent by mass, on the average of 4.5 percent by mass. The materials customarily used in breast-milk absorbent pads, that is to say, fiber material on a cellulose base and optional superabsorbent hydrogel material, absorb only the aqueous part of the reflowing mother's milk. The fatty part remains unabsorbed; this means that it adheres to surfaces of the absorbent materials. This causes a reduction in the active surface available for absorbing fluid, and the efficacy of the absorption process is interrupted or reduced. The result of this can be that after a certain time, and depending on the reflowing mother's milk, it can no longer be absorbed effectively, but runs down from the absorbent materials.

DETAILED DESCRIPTION

Figure 1:
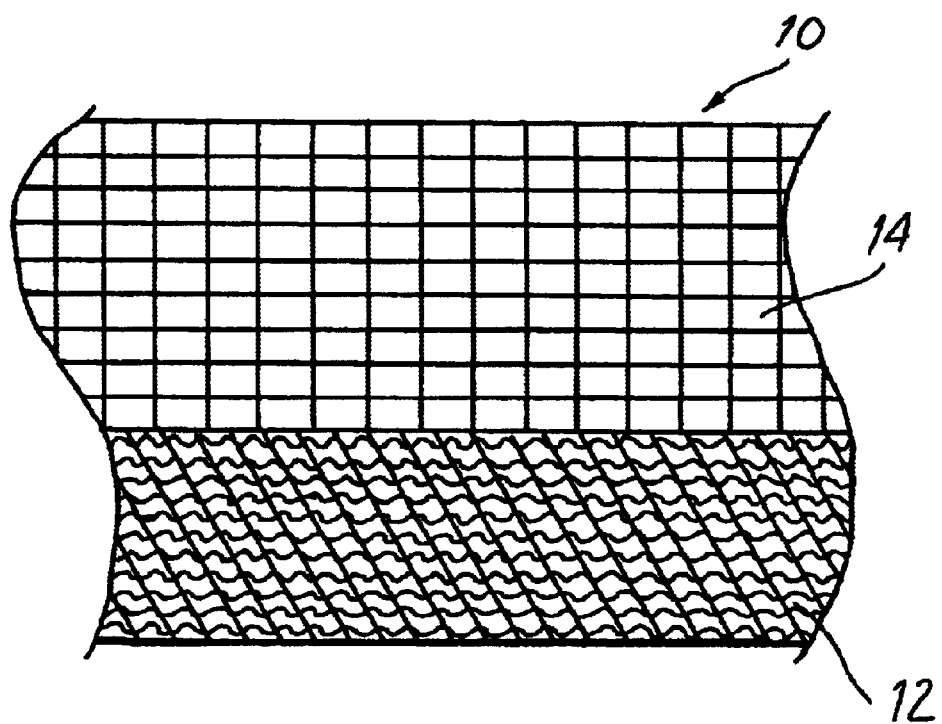
FIG. 1 is a cross sectional view of a breast milk absorbent pad according to the present invention.

From this point of departure, the desire of the present invention is to improve a breast-milk absorbent pad 10 of the type named above, in such a way that the previously described disadvantages can be overcome and the available fluid absorbency capacity of the breast-milk absorbent pad 10 can be better utilized. This desire is achieved by means of a breast-milk absorbent pad 10 of the type named in accordance with the invention which additionally comprises chitosan.

Chitosan is a natural material, to be precise a biopolymer, which can be obtained from chitin, the shell of crustaceans, specifically by deacetylation. It can be produced in the form of a powder or in fiber form and introduced into the breast-milk absorbent pad.

It is known that chitosan can be used as an effective fat absorber (D. Heinrichs, Manual of "Nutrients and Vital Materials," M-Z Verlag). In addition it is known how to produce chitosan derivatives in a practically endless variety and to use them as adsorbents, for example, for heavy metals, which is described in JP 61-133143-A.

DE 43 18 094 A1 teaches the use of chitosan converted with acid as a superabsorbent means in a hygiens article. It is primarily concerned with its ability to absorb urine.

In a quite particularly advantageous manner, chitosan occurring in nature as a biopolymer is naturally degradable. If the remaining components of the breast-milk absorbent pad 10 are constructed in the form of an outer layer 14 facing away from the body in use and the layer 12 facing towards the body in use made of biodegradable materials, the breast-milk absorbent pad 10 can be offered as a compostable product. For the fluid-permeable layer 12 facing the body, a viscose fiber material can preferably be selected and, for the outer layer 14, a fiber material or a viscose-based film, PVA (polyvinyl alcohol), polyester amide, starch-copolyester, starch/polycaprolactam mixture, copolymers of polyhydroxy butyric acid (PHB) and polyhydroxy valeric acid (PLA). The outer layer 14 can also be a hydrophobic fabric material, for example, polypropylene can be used.

The chitosan can also be located in the layer 12 facing against the body, that is, in direct body contact. It is proving advantageous in the meantime if the chitosan is located in the absorbent layer 12 proper. This absorbent layer 12 is formed advantageously from 1–5 grams, preferably from 2–4 grams, of fluffy material manufactured on a cellulose base. It can also comprise superabsorbent polymer materials. In this case, the absorbent layer 12 is advantageously composed of 1.5–2.5 grams of fluffy material and 0.5–1.5 grams of superabsorbent polymer material.

It has proven to be advantageous and adequate if 0.2–1 gram of chitosan is used for each breast-milk absorbent pad 10.

The percentage amount by mass of chitosan in the absorbent layer 12 advantageously amounts to between 5 and 25 percent.

What is claimed is:

1. A breast-milk absorbent pad having a fluid-absorbent layer formed of a fiber material, characterized in that the absorbent layer additionally contains 0.2–1.0 grams of chitosan.

2. The breast-milk absorbent pad in accordance with claim 1, wherein the absorbent layer contains 1.0–5.0 grams of fluffy material.

3. The breast-milk absorbent pad in accordance with claim 2, wherein the absorbent layer comprises 1.5–2.5 grams of fluffy material and 0.5–1.5 grams of superabsorbent polymer materials.

4. The breast-milk absorbent pad in accordance with claim 1, wherein the percentage by mass of the chitosan in the absorbent layer amounts to 5–25 percent.

5. The breast-milk absorbent pad in accordance with claim 1 characterized by an external layer in the form of one of a hydrophobic fabric material, a film and a fabric-film laminate facing away from a body in use.

6. The breast-milk absorbent pad in accordance with claim 1, characterized by a fluid-permeable layer of one of viscose and viscose/polyester facing a body in use.

7. The breast-milk absorbent pad in accordance with claim 1 wherein the absorbent layer is formed only of completely biodegradable materials.

8. The breast-milk absorbent pad in accordance with claim 1 wherein the absorbent layer contains superabsorbent hydrogel materials.

9. The absorbent pad in accordance with claim 2, wherein the absorbent layer contains 2.0–4.0 grams of fluffy material.

* * * * *

UNITED STATES PATENT AND TRADEMARK OFFICE
CERTIFICATE OF CORRECTION

PATENT NO. : 6,676,645 B1
DATED : January 13, 2004
INVENTOR(S) : Andreas Bitterhof It is certified that error appears in the above-identified patent and that said Letters Patent is hereby corrected as shown below:

Cover Page,
Item [73], Assignee, replace "[Paul-Hartmann-Strasse AG,] with -- Paul Hartmann AG --.

Signed and Sealed this

Eighth Day of June, 2004

JON W. DUDAS
*Acting Director of the United States Patent and Trademark Office*